United States Patent [19]
Gielen et al.

[11] Patent Number: 5,583,157
[45] Date of Patent: Dec. 10, 1996

[54] DIBUTYLTIN BIS(DIHYDROXYBENZOATES) AND COMPOSITIONS CONTAINING THESE COMPOUNDS

[75] Inventors: Marcel Gielen, Weezenbeek-Oppem; Rudolph Willem, Vilvoorde; Abdeslam Bouhdid, Brussel, all of Belgium; Dick de Vos, Oegstgeest, Netherlands

[73] Assignee: Pharmachemie B.V., Haarlem, Netherlands

[21] Appl. No.: 420,557

[22] Filed: Apr. 12, 1995

[30] Foreign Application Priority Data

Apr. 12, 1994 [EP] European Pat. Off. ............ 94201012

[51] Int. Cl.$^6$ .............................. A61K 31/32; C07F 7/22
[52] U.S. Cl. .................. 514/493; 556/90; 556/94; 556/106
[58] Field of Search ................. 556/90, 94, 106; 514/493

[56] References Cited

FOREIGN PATENT DOCUMENTS

| | | |
|---|---|---|
| 0472783 | 3/1992 | European Pat. Off. . |
| 0484596 | 5/1992 | European Pat. Off. . |
| 0538517 | 4/1993 | European Pat. Off. . |

OTHER PUBLICATIONS

Chemical Abstracts, vol. 77, No. 14, 2 Oct. 1972, Columbus, Ohio, US; abstract No. 93565r, Zaitsev, P. M. et al, 'Complexes of Tin Tetrachloride with Aromatic Acids', p. 370; & Zh. Obshch. Khim., vol. 42, No. 7, 1972, pp. 1509–1513.

Chemical Abstracts, vol. 71, No. 7, 18 Aug. 1969, Columbus, Ohio, US; abstract No. 29139d, Murakumi, H. et al, 'Antitumor Activities of Polyphenols', p. 169; & Kyushu Daigaku Nogakubu Gakugei Zasshi, vol. 24, No. 1, 1969, pp. 19–24.

*Primary Examiner*—Porfirio Nazario-Gonzales
*Attorney, Agent, or Firm*—Browdy and Neimark

[57] ABSTRACT

This invention provides novel Sn compounds, i.e. di-n.butyltindihydroxybenzoates, which exhibit excellent activities against varies tumors. This invention also provides pharmaceutical compositions which contain said novel Sn compounds in combination with a suitable carrier, in particular aqueous solutions which are suitable for injection.

6 Claims, No Drawings

DIBUTYLTIN BIS(DIHYDROXYBENZOATES) AND COMPOSITIONS CONTAINING THESE COMPOUNDS

FIELD OF THE INVENTION

The present invention provides novel compounds of the formula

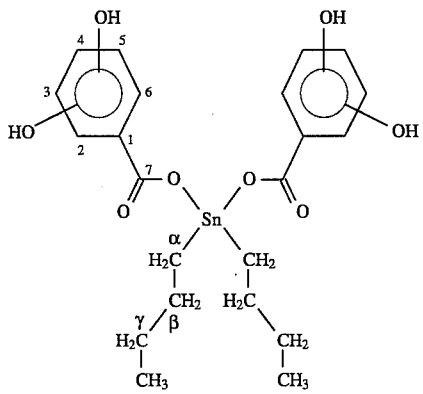

which compounds show a strong anti-tumour activity.

This invention also provides anti-tumour compositions, containing a compound as defined above in combination with a suitable carrier.

SUMMARY OF THE INVENTION

The di-n.butylin derivative of 3-methoxysalicylic acid, bis[2-hydroxy-3-methoxybenzoato(di-n.butyl)tin]oxide, $[2\text{-OH-}3\text{-CH}_3\text{OC}_6\text{H}_3\text{COOSnBu}_2)_2\text{O}]_2$, exhibits an enhanced antitumour activity in vitro against MCF-7, a mammary tumour, and WiDr, a colon carcinoma, as compared to the 5-methyl- and 4-methoxy substituted analogs. Thus, it is characterized by $ID_{50}$ values of 29 and 122 ng/ml, respectively, while the 5-methyl analogue exhibits values of 90 and 337 ng/ml and the 4-methoxy analogue shows values of 1800 ng/ml. (M. Gielen, P. Lelieveld, D. de Vos and R. Willem, "In vitro antitumour activity of organotin compounds", Chapter II of "Metal-Based Antitumour Drugs", M. Gielen, Ed., Freund Publishing House, London (1992), pages 29–54.

Also the position of the substituents may influence the antitumour activity of the di-n.butyltin bis(methoxysalicylates) $(CH_3O\text{-}2\text{-OH-}C_6H_3COO)_2SnBu_2$; the 4-methoxy derivative shows $ID_{50}$ values of 131 and 1182 ng/ml, while for the 5-methoxy derivative these values are 54 and 611 ng/ml, respectively. Di-n.butyltin bis(4-hydroxy-3-methoxy-benzoate), $(4\text{-OH-}3\text{-CH}_3O\text{-}C_6H_3COO)_2SnBu_2$ exhibits comparatively very low $ID_{50}$ values (44 ng/ml and 82 ng/ml, respectively) (M. Gielen, P. Lelieveld, D. de Vos and R. Willem, ibid.)

The $ID_{50}$ value is the concentration of the drug (in ng/ml) at which 50% growth inhibition occurs.

The above defined compounds according to this invention were tested for their anti-tumour activities and were found to have excellent properties in this respect.

The present compounds, which have the general formula $[(HO)_2C_6H_3COO]_2Sn(n\text{-}C_4H_9)_2$, were synthesized from the corresponding dihydroxybenzoic acid and di-n.butyltin oxide in a 2:1 molar ratio, using the following procedure: the appropriate dihydroxybenzoic acid, $(HO)_2C_6H_3COOH$, is dissolved in a 4:1 mixture of toluene and ethanol. The diorganotin oxide is added to this solution in a molar ratio acid to diorganotin oxide of 1:1 or 2:1. The reacting mixture is refluxed for 4 to 6 h. The ternary azeotrope/-water/ethanol/toluene followed by the binary azeotrope ethanol/toluene are distilled off with a Dean-Stark funnel to 50% reduction of the initial volume. The remaining solution is evaporated under reduced pressure. The solid or oil obtained is purified by recrystallization in appropriate solvents.

DETAILED DESCRIPTION OF THE INVENTION

CHARACTERIZATION

Di-n.butyltin 2,3-dihydroxybenzoate, Compound 1 m.p.: >350° C., yield: 93%; Mössbauer parameters (in mm/s): QS: 3.84, IS: 1.43, $\Gamma_1\&\Gamma_2$: 1.00&0.97; $^1$H NMR (DMSO-$d_6$) parameters: H-4: dd, 6.70 [8, 1]; H-5: dd, 6.42 [8, 8]; H-6: dd, 6.88 [8, 1]: $CH_2$-α: m, 1.43–1.52; $CH_2$-β: m, 1.30–1.42; $CH_2$-.tq, 1.19 [7, 7]; $CH_3$: t, 0.75 [7]; OH: s, 13.7; $^{13}$C NMR (DMSO-$d_6$): C-1: 113.6; C-2 & C-3: 155.5 & 153.1: C-4, C-5 & C-6: 116.4, 117.0 & 117.1; C-7: 167.6; C-α: 26.2 [$^1$J(C-Sn): 686]; C-β: 26.4 [$^2$J(C-Sn): 39]; C-.25.5 [$^3$J(C-Sn): 110]; $CH_3$: 13.4; $^{119}$Sn NMR (DMSO-$d_6$): −171.6

Di-n.butyltin 2,4-dihydroxybenzoate, Compound 2

Recrystallized from $CHCl_3$: m.p.: >350° C., yield: 94%; Mössbauer: QS: 3.69, IS: 151, $\Gamma_1\&\Gamma_2$: 0.92 & 0.99; $^1$H NMR ($CDCl_3$): H-3: d, 6.42 [2]; H-5: dd, 6.41 [8, 2]; H-6: d, 7,86 [8]; $CH_2$-α& $CH_2$-β: m, 1.65–1.86; $CH_2$-.tq, 1.39 [7, 7]; $CH_3$: t, 0.89 [7]; OH: bs, 10.8; $^{13}$C NMR ($CDCl_3$): C-1: 105.8; C-2 & C-4: 163.4 & 162.6; C-3: 103.0; C-5: 108.0; C-6: 133.5; C-7: 177.1; C-α: 26.4 [$^1$J(C-$^{119/117}$Sn): 564/538]; C-β: 26.5 [$^2$J(C-Sn): 34]; C-: 26.3 [$^3$J(C-Sn): 97]; $CH_3$: 13.3; $^{119}$Sn NMR (DMSO-$d_6$): −256.1; ($CDCl_3$): −125.6

Di-n.butyltin 2,5-dihydroxybenzoate, Compound 3

Recrystallized from $CHCl_3$: m.p.: 116°–118° C., yield: 96%; Mössbauer: QS: 3.72, IS: 1.53, $\Gamma_1\&\Gamma_2$: 1.09 & 0.84; $^1$H NMR ($CDCl_3$): H-3: d, 6.90 [9]; H-4: dd, 7.06 [9, 3]; H-6: d, 7,41 [3]; $CH_2$-α:t, 1.87 [7]; $CH_2$-β: tt, 1.71 [7, 7]; $CH_2$-.tq, 1.39 [7, 7]; $CH_3$: t, 0.89 [7]; OH: bs, 10.2; $^{13}$C NMR ($CDCl_3$): C-1: 112.3; C-2 & C-5: 155.7 & 147.9; C-3: 116.0; C-4 & C-6: 124.5 & 118.4; C-7: 177.1; C-α: 26.4 [$^1$J(C-$^{119/117}$Sn): 572/546]; C-β: 26.3 [$^2$J(C-Sn): 32]; C-: 26.2 [$^3$J(C-Sn): 98]; $CH_3$: 13.3; $^{119}$Sn NMR (DMSO-$d_6$): −240.1; ($CDCl_3$): −121.8

Di-n.butyltin 2,6-dihydroxybenzoate, Compound 4

Recrystallized from $CHCl_3$: m.p.: 121°–122° C., yield: 92%; Mössbauer: QS: 4.66, IS: 1.59, $\Gamma_1\&\Gamma_2$: 0.92 & 0.91; $^1$H NMR ($CDCl_3$): H-3 & H-5: d, 6.50 [8]; $CH_2$-α: t, 1.96 [7]; $CH_2$-β: tt, 1.75 [7, 7]; $CH_2$-.tq, 1.41 [7, 7]; $CH_3$: t, 0.93 [7]; OH: bs, 10.1; $^{13}$C NMR ($CDCl_3$): C-1: 99.6; C-2 & C-6: 161.8; C-3 & C-5: 107.9; C-4: 137.4; C-7: 178.3; C-α: 28.0 [$^1$J(C-$^{119/117}$Sn): 554/528]; C-β: 26.6 [$^2$J(C-Sn): 36]; C-: 26.5 [$^3$J(C-Sn): 100]; $CH_3$: 13.4; $^{119}$Sn NMR (DMSO-$d_6$): −377.2; ($CDCl_3$): −122.3

Di-n.butyltin 3,4-dihydroxybenzoate, Compound 5

Recrystallized from ethanol/cyclohexane; m.p.: >350° C., yield: 91; Mössbauer: QS: 3.66, IS: 1.42, $\Gamma_1\&\Gamma_2$: 0.90 & 0.93; $^1$H NMR (DMSO-$d_6$): H-2: d, 7.28 [2]; H-5: d, 6.72 [8]; H-6: dd, 7.23 [8, 2] $CH_2$-α: t, 1.48 [8]; $CH_2$-β: tt, 1.23

[8, 8]; CH$_2$-.m, 1.01–1.13; CH$_3$: t, 0.75 [8]; OH: bs, 11.8; $^{13}$C NMR (DMSO-d$_6$): C-1: 121.7; C-2, C-5 & C-6: 116.4, 117.6 & 119.9; C-3: 144.6; C-4: 149.7; C-7: 168.6; C-α: 24.6 [$^1$J(C-$^{119/117}$Sn): 656/625]; C-β: 25.6 [$^2$J(C-Sn): 36]; C-: 26.3; CH$_3$: 13.3; $^{119}$Sn NMR (DMSO-d$_6$): –134.4

Di-n.butyltin 3,5-dihydroxybenzoate, Compound 6

Recrystallized from ethanol; m.p.: 222°–224° C., yield: 85; Mössbauer: QS: 3.38, IS: 1.44, Γ$_1$&Γ$_2$: 0.96 & 1.02; $^1$H NMR (DMSO-d$_6$): H-2 & H-6: d, 6.76 [2]; H-4: t, 6.33 [2]; H-6: dd, 7.23 [8, 2] CH$_2$-α& CH$_2$-β: m, 1.35–1.51; CH$_2$-: tq, 1.22[7, 7]; CH$_3$: t, 0.73 [7]; OH: bs, 9.4; $^{13}$C NMR (DMSO-d$_6$): C-1: 132.6; C-2 & C-6: 106.7; C-3 & C-5: 157.3; C-4: 105.5; C-7: 171.8; C-α: 28.6 [$^1$J(C-$^{119/117}$Sn): 852/812]; C-β: 25.8 [$^2$J(C-Sn): 40]; C-: 24.6 [$^3$J(C-Sn): 135]; CH$_3$: 12.6; $^{119}$Sn NMR (DMSO-d$_6$): –344.3

In Vitro Antitumour Tests

Compounds 1 to 4 were screened in vitro against several human tumour cell lines: MCF-7 and EVSA-T, two breast cancers, WiDr, a colon cancer, IGROV, an ovarian cancer, M19 MEL, a melanoma and A498, a renal cancer. MCF-7 is estrogen receptor ER+/Progesterone receptor PgR+, and EVSA-T is ER–/Pgr–. The other four cell lines belong to the currently used anti-cancer screening panel of the National Cancer Institute, Bethesda, Md., U.S.A.

The compounds were tested in quadruple at 10 concentrations varying with a factor 3, ranging from 3 to 59050 ng/ml.

Concentration response curves were determined and the ID$_{50}$ (drug concentration in ng/ml at 50% growth inhibition) values were calculated.

Prior to the experiments a mycoplasma test was carried out on all cell lines and found to be negative. All cell lines, except EVSA-T, were maintained in a continuous logarithmic culture in RPMI medium with Hepes and Phenol red supplemented with 10% bovine calf serum (BCS), penicillin 111 IU/ml, streptomycin 111 μg/nl, gentamycin 46 μg/ml and insulin 10.6 μg/ml. EVSA-T was maintained in DMEM with 5% BCS and antibiotics as described. The cells were mildly trypsinized for passage and for use in experiments.

RPMI, DMEM and SrB (sulforhodamine B) were obtained from Brunschwig (Amsterdam, The Netherlands). BCS was obtained from Hyclone (Logane, Utah, U.S.A.), DMSO from Baker (Deventer, The Netherlands), phosphate-buffered saline (PBS) from Boom (Meppel, The Netherlands), insulin Neerlandicum from Organon (Oss, The Netherlands). Streptomycin, penicillin, gentamycin and trypsin were obtained from Gibco (Breda, The Netherlands).

The test and reference compounds were dissolved in a concentration of 177147 ng/ml as follows:
Organotin compounds: 1.0 to 2.2% DMSO in full growth RPMI medium.
Carboplatin: 10% water in full growth RPMI medium
Cis-platin: 0.17% DMSO in full growth RPMI medium No additional pretreatment such as ultra sonication, was needed for a complete dissolution of all compoumds.

On day 1, 200 μl of trypsinized tumor cells (2000 cells/well) were plated in 96-wells flatbottom microtiter plates (Costar, no. 3799, Badhoevedorp, The Netherlands). The plates were preincubated for 24 hr at 37° C., 5% CO$_2$ to allow the cells to adhere.

On day 2, 100 μl of a solution with the highest drug concentration were added to the well of column 12 and from there diluted 3-fold to column 3 by serial transfer of 100 μl using an 8 channel micropipette. The final volume of column 3 was adjusted to 200 μl with PBS. Column 2 was used as a blank. PBS was added to column 1 tot diminish interfering evaporation.

On day 7 the incubation was terminated by washing the plates twice with PBS. Subsequently the cells were fixed with 10% trichloroacetic acid in Milli Q water (Millipore, Etten Leur, The Netherlands) and placed at 4° C. for one hour.

After five washings with tap water, the cells were stained for at least 15 min with 0.4% SRB, dissolved in 1% acetic acid, and subsequently washed with 1% acetic acid to remove the unbound stain. The plates were air dried and the bound protein stain was dissolved by using 150 μl 10 mmol/l tris base. The absorbance was read at 540 nm using an automated microplate reader (Titertec, Flow Laboratories Ltd., Irvine, Scotland).

The ID$_{50}$ values in ng/ml obtained for these compounds, shown in the following table, are compared to the cytotoxicities of two common drugs i.e. carboplatin and cisplatin.

The table indicates all the organotin compounds tested to be more active in vitro against all cell lines than carboplatin and cisplatin

TABLE

|   | MCF-7 Breast Cancer | EVSAT Breast Cancer | WiDr Colon Cancer | IGROV Ovarian Cancer | M19 Melanoma | A498 Renal Cancer |
| --- | --- | --- | --- | --- | --- | --- |
| 1) 2,3-(OH)$_2$C$_6$H$_3$COO]$_2$SnBu$_2$ | 7 | 43 | 90 | 51 | 50 | 50 |
| 2) 2,4-(OH)$_2$C$_6$H$_3$COO]$_2$SnBu$_2$ | 16 | 54 | 120 | 85 | 58 | 130 |
| 3) 2,5-(OH)$_2$C$_6$H$_3$COO]$_2$SnBu$_2$ | 4 | 48 | 115 | 60 | 65 | 100 |
| 4) 2,6-(OH)$_2$C$_6$H$_3$COO]$_2$SnBu$_2$ | 15 | 58 | 130 | 110 | 65 | 130 |
| Carboplatin | 5500 | 1100 | 1500 | 780 | 5300 | 3500 |
| Cisplatin | 800 | 1200 | 650 | 79 | 530 | 1200 |

The present invention also provides compositions, in particular injectable compositions, containing a novel Sn compound of this invention and carrier therefor, in particular a liquid carrier, such as water; in addition to water an alcohol, glycerol and the like can be present. Furthermore, such compositions may contain adjuvants such as sugars (mannitol, sorbitol, lactose, glucose, etc.), salts (e.g. sodium chloride), buffers (e.g. phosphate buffer), preservatives etc.

We claim:

1. A Dibutyltin bis(dihydroxybenzoate) of the formula:

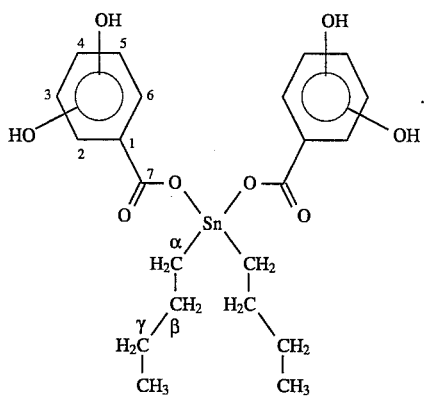

2. A composition for treating tumors comprising a compound according to claim 1 and a pharmaceutically acceptable carrier.

3. A composition according to claim 2 further containing additives.

4. A composition according to claim 2 wherein said pharmaceutically acceptable carrier is water.

5. A method for controlling malignant tumors in mammals comprising administering to a mammal suffering from a malignant tumor an effective amount of a compound according to claim 1.

6. A method for preparing a dibutyltin bis(dihydroxybenzoate) of the formula:

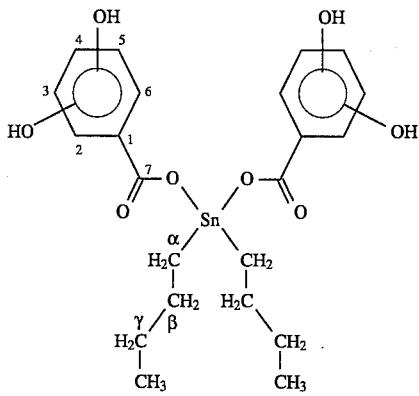

comprising reacting di-n-butyltin oxide with a dihydroxybenzoic acid in a molar ratio of from 1:1 to 1:2; and recovering said dibutyltin bis(dihydroxybenzoate).

* * * * *